United States Patent
Wang et al.

(10) Patent No.: US 11,161,851 B2
(45) Date of Patent: Nov. 2, 2021

(54) PROCESSES TO PRODUCE ACALABRUTINIB

(71) Applicant: SUZHOU PENGXU PHARMATECH CO., LTD., Suzhou (CN)

(72) Inventors: Peng Wang, Scotch Plains, NJ (US); Pixu Li, Suzhou (CN); Xiangyong Gu, Suzhou (CN); Yadong Ge, Suzhou (CN); Zhong Wang, Suzhou (CN); Feng Gao, Suzhou (CN); Qiangqiang Du, Suzhou (CN)

(73) Assignee: Suzhou PengXu Pharmatech Co. Ltd., JiangSu (CN)

( * ) Notice: Subject to any disclaimer, the term of this patent is extended or adjusted under 35 U.S.C. 154(b) by 43 days.

(21) Appl. No.: 16/762,122

(22) PCT Filed: Nov. 5, 2018

(86) PCT No.: PCT/US2018/059280
§ 371 (c)(1),
(2) Date: May 6, 2020

(87) PCT Pub. No.: WO2019/090269
PCT Pub. Date: May 9, 2019

(65) Prior Publication Data
US 2020/0354368 A1    Nov. 12, 2020

(30) Foreign Application Priority Data

Nov. 6, 2017 (CN) .......................... 201711078254.5
Nov. 27, 2017 (CN) .......................... 201711209514.8

(51) Int. Cl.
| C07D 471/02 | (2006.01) |
| C07D 471/04 | (2006.01) |
| C07D 487/04 | (2006.01) |
| C07D 213/75 | (2006.01) |
| C07D 403/12 | (2006.01) |
| C07F 5/02 | (2006.01) |

(52) U.S. Cl.
CPC .......... *C07D 487/04* (2013.01); *C07D 213/75* (2013.01); *C07D 403/12* (2013.01); *C07F 5/025* (2013.01)

(58) Field of Classification Search
CPC ................ C07D 471/02; C07D 471/04; C07D 487/04
See application file for complete search history.

(56) References Cited

FOREIGN PATENT DOCUMENTS

| WO | 2013/010868 A1 | 1/2013 |
| WO | 2014/019344 A1 | 2/2014 |
| WO | 2015/048689 A1 | 4/2015 |

OTHER PUBLICATIONS

Supplemental European International Search Report dated Mar. 23, 2021 for related EP Application No. EP18873306.7.
Berg Stefan et al: "Discovery of Novel Potent and Highly Selective Glycogen Synthase Kinase-3[beta] (GSK3 [beta]) Inhibitors for Alzheimer's Disease: Design, Synthesis, and Characterization of Pyrazines—Supporting information", Journal of Medicinal Chemistry American Chemical Society, vol. 55, No. 21, Jan. 1, 2012.

*Primary Examiner* — Bruck Kifle
(74) *Attorney, Agent, or Firm* — Enshang Hong; MagStone Law, LLP

(57) ABSTRACT

The present invention relates to a method for preparing the compound of formula IV, compound of formula XI, and acalabrutinib, a new generation of bruton tyrosine kinase (BTK) inhibitor.

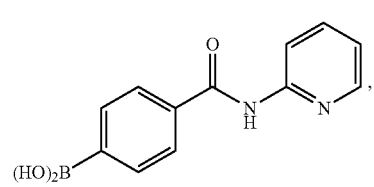

IV

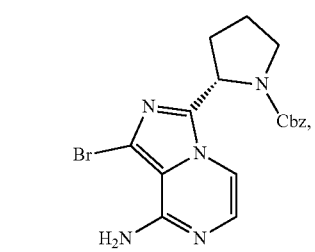

XI

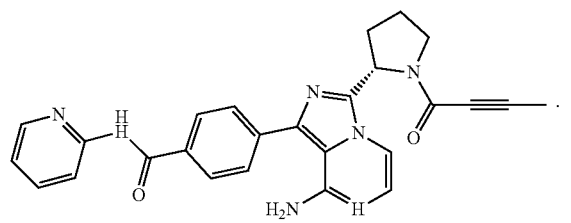

XV (Acalabrutinib)

23 Claims, No Drawings

PROCESSES TO PRODUCE ACALABRUTINIB

BACKGROUND OF THE INVENTION

1. Field of the Invention

The present invention relates to a method for preparing the compound of formula IV, compound of formula XI, and acalabrutinib, a new generation of bruton tyrosine kinase (BTK) inhibitor.

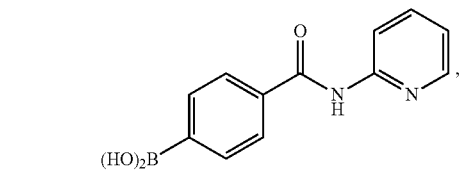

IV

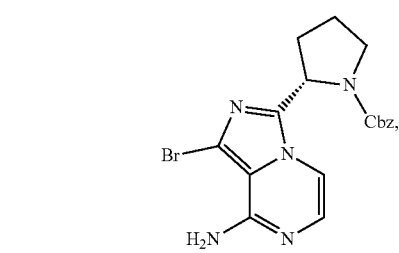

XI

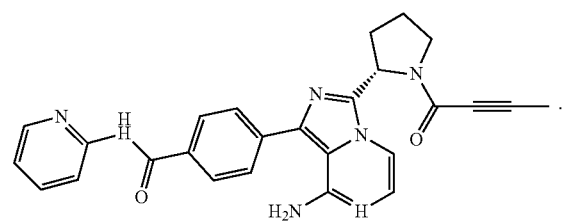

XV (Acalabrutinib)

2. Description of the Related Art

Calquence (acalabrutinib; previously known as ACP-196) is a selective inhibitor of BTK. Calquence binds covalently to BTK, thereby inhibiting its activity, and has demonstrated this with minimal interactions with other immune cells in pre-clinical studies.

Calquence is also in development for the treatment of multiple B-cell malignancies and other cancers including chronic lymphocytic leukaemia (CLL), mantle cell lymphoma (MCL), Waldenström macroglobulinaemia (WM), follicular lymphoma, diffuse large B-cell lymphoma, and multiple myeloma. It is also being studied as a monotherapy and in combination trials for solid tumours. More than 35 clinical trials across 40 countries with more than 2,500 patients are underway or have been completed.

Calquence was granted Orphan Drug Designation by the US FDA for the treatment of adult patients with MCL in September 2015 and by the European Commission in March 2016 for the treatment of adult patients with CLL, MCL and WM. Calquence was granted Breakthrough Therapy Designation by the FDA in August 2017 and it was approved in Oct. 31, 2017 for the treatment of adult patients with MCL who have received at least one prior therapy.

The preparation of acalabrutinib was disclosed in International Patent Application WO2013/010868A1:

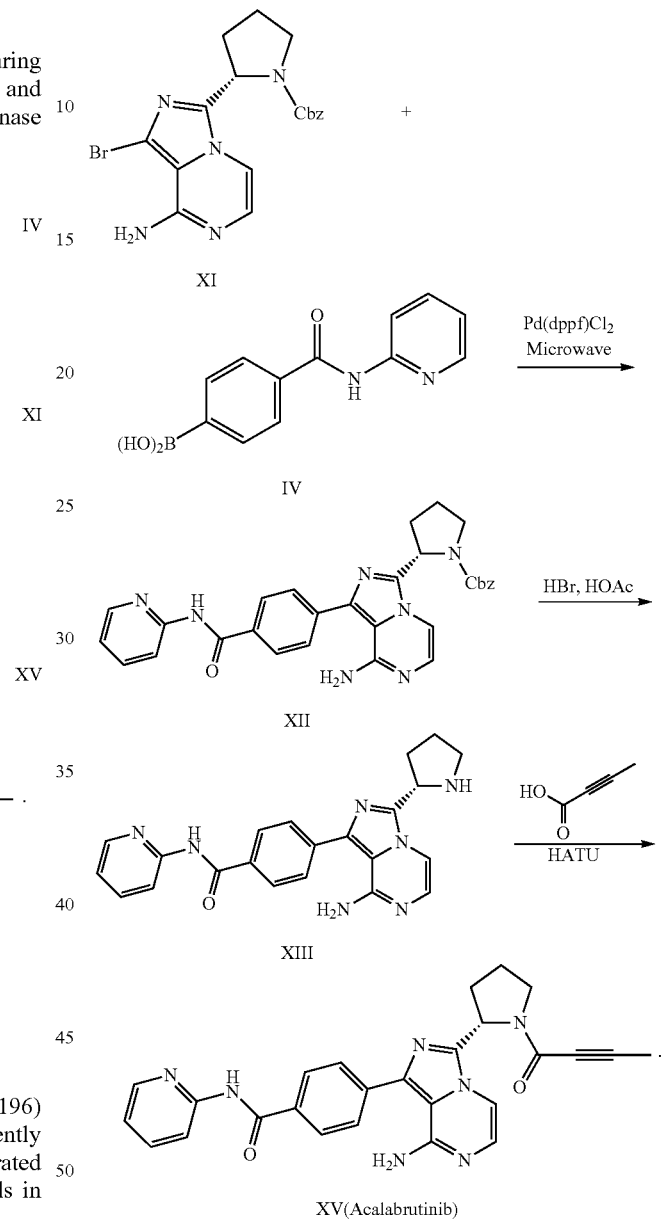

Compound XI is a key intermediate for the preparation of acalabrutinib, and the synthetic route of Compound XI was also disclosed in International Application WO2013/010868A1:

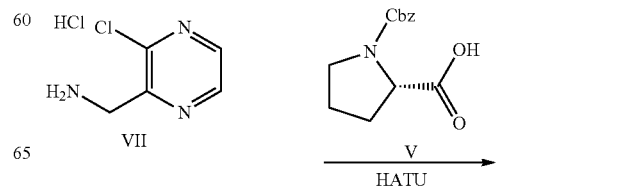

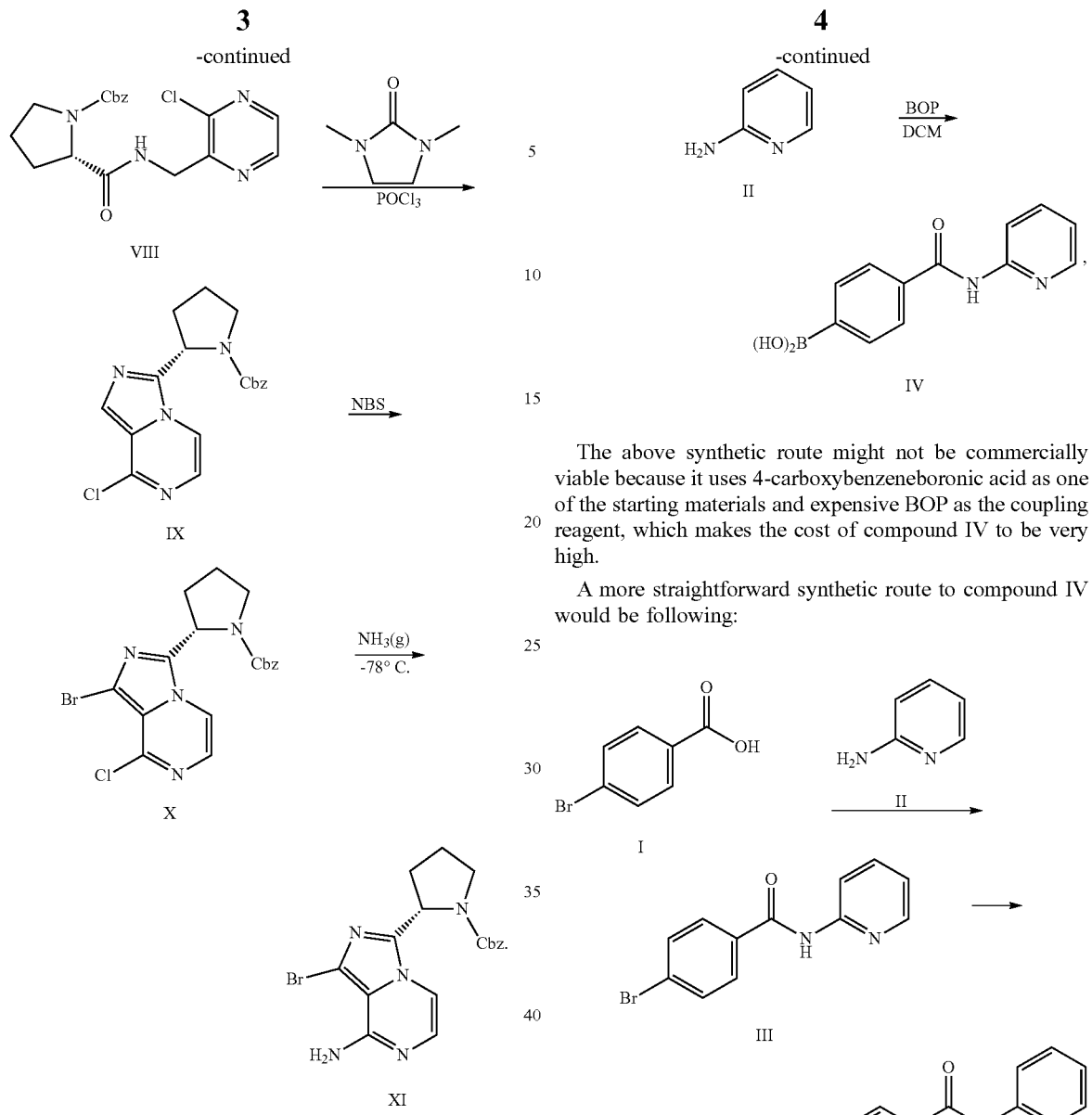

The above synthetic route might not be commercially viable because it uses 4-carboxybenzeneboronic acid as one of the starting materials and expensive BOP as the coupling reagent, which makes the cost of compound IV to be very high.

A more straightforward synthetic route to compound IV would be following:

The technical solution for the preparation of compound VIII in WO2013/010868A1 requires the use of the expensive reagent, HATU, resulting in high raw material cost. Meanwhile, the process for the preparation of the compound XI requires temperature at −78° C. and involves the use of ammonia gas, which is not ideal for scale-up production.

Compound IV is the other key intermediate for the preparation of acalabrutinib. The synthetic route of Compound IV was disclosed in Bioorganic & Medicinal Chemistry Letters 16 (2006), 5217-5221:

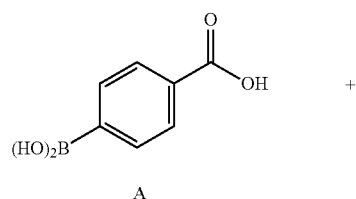

Nevertheless, the synthetic route has several technical problems.

1) the synthesis of Compound III via amide bond formation of compound I and compound II is much more difficult than it appears due to the low nucleophilicity of amino group of the 2-aminopyridine. The synthesis of compound III was disclosed in WO2015/048689A1 and WO2015/104722A1 with only 65% and 45% yields, respectively. In Tetrahedron Letters 50 (2009), 1986-1988, the authors clearly pointed out "When the acylations are attempted with weakly nucleophilic amines, however, they are often met with long reaction times and harsh conditions. . . . Although there is ample literature precedent for carboxylic acid couplings with 2-aminopyridines, the yields tend to be quite variable and more often than not, require transformation to the acid chloride prior to coupling."

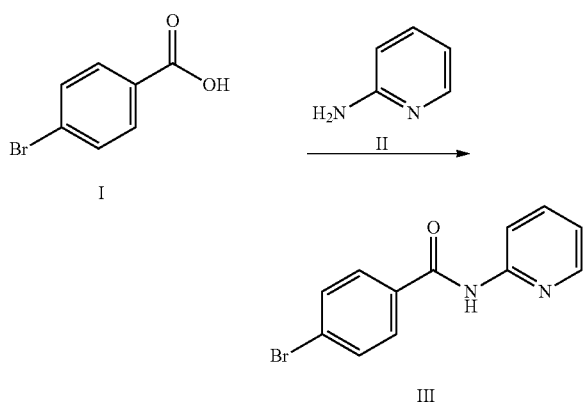

| Entry | Literature | Reaction condition | Yield |
|---|---|---|---|
| 1 | WO2015048689 | 1. (COCl)$_2$, DMF, DCM; 2. Compound II, Py, DCM | 65% |
| 2 | WO2015104722 | EDCl, HOBt, DCM | 45% |

Attempts following the example in WO2015/048689A1 only provided compound III in very low yield with a lot of by-product B in process in our laboratory.

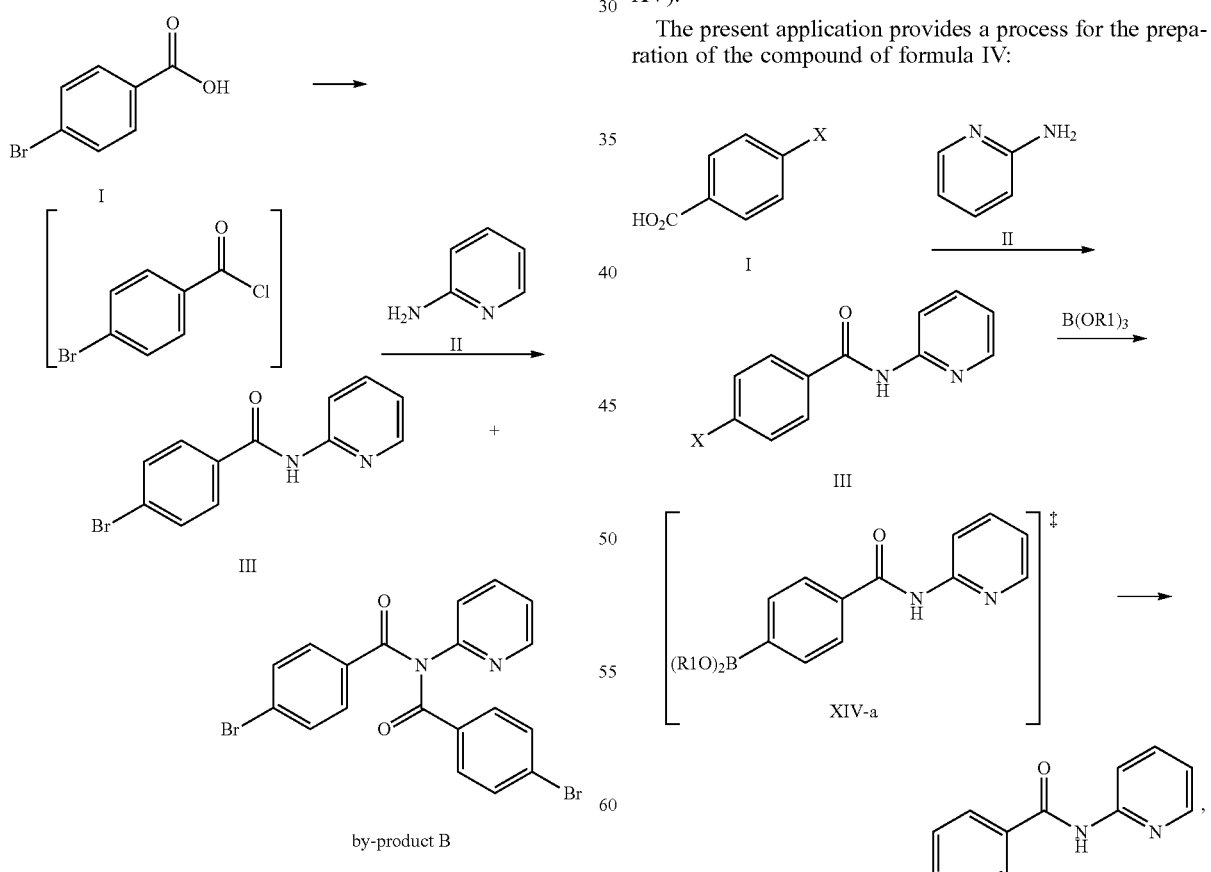

2) The conversion of aryl bromide to the corresponding boronic acid usually involves halogen-metal exchange with either organolithium reagent or Grignard reagent followed by reaction with trialkyl borate. However, in the case of compound III, the formation of the corresponding organometallic compound by halogen-metal exchange is extremely difficult, as the organometallic compound would be self-quenched by the acidic proton of the amide.

Technical Problem

The current processes to the intermediates of acalabrutinib, compound IV and compound XI require tedious purification, special equipment, high raw material cost, and low yield. A scalable preparation route is needed to overcome the problems for large-scale production.

SUMMARY OF THE INVENTION

It is the object of the present invention to provide a cost effective and scalable process for the preparation of acalabrutinib and two intermediates, compound of formula IV and compound of formula XI.

One purpose of the present application is to provide a preparation of compound IV.

A further purpose of the present application is to provide a method to prepare of compound XI.

A further purpose of the present application is to provide a process to prepare of acalabrutinib (compound of formula XV).

The present application provides a process for the preparation of the compound of formula IV:

Wherein R1 is a substituent selected from the group consisting of C1-20 alkyl or benzyl, preferably methyl, ethyl, propyl, isopropyl and benzyl; X is Br or I. More preferably, wherein R1 represents substituent is isopropyl group; X is Br.

In a specific embodiment, the reaction conditions for each reaction step are detailed below:

Synthesis the Compound of Formula III from the Compound of Formula I and Compound of Formula II:

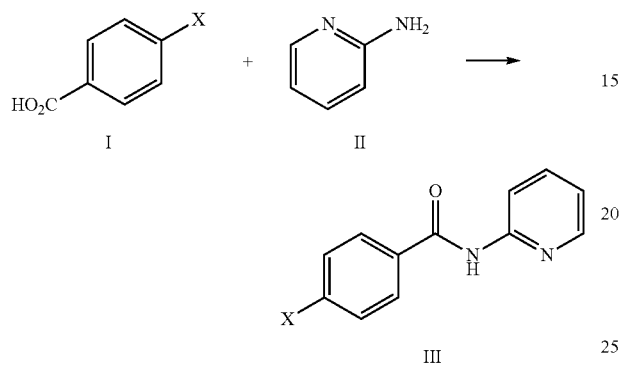

Many methods and coupling reagents are known for the formation of amide from a carboxylic acid and an amine, such as via acid halide or using coupling reagents like EDCl and HATU. However, the formation of amide from compound II is known to be difficult because the low nucleophillic nature of compound II [Tetrahedron Letters 50 (2009) 1986-1988]. In all the literature reported, amide formation of compound II afforded compound III in low yields [(a) Tetrahedron 64 (2008), 6230-6237; (b) J. Org. Chem. 67 (2002), 8832-8841; (c) J. Med. Chem. 50 (2007), 1850-1864]. After many failed trials, it was unexpectedly discovered that the use of special carboxylic acid activating reagents afforded high yield of the desired amide. The activating reagent is selected from N,N'-carbonyldiimidazole, methanesulfonyl chloride, p-toluenesulfonyl chloride and p-nitrobenzene sulfonyl chloride. The reaction solvent is selected from N,N-dimethylformamide, N,N-dimethylacetamide, acetonitrile, tetrahydrofuran, methyltetrahydrofuran, toluene, xylene, dioxane, dimethyl sulfoxide, N-methylpyrrolidone, sulfolane, methylene chloride and mixtures thereof. More preferably, wherein, the solvent selected from tetrahydrofuran, toluene, dioxane.

Synthesis of the Compound of Formula IV from the Compound of Formula III:

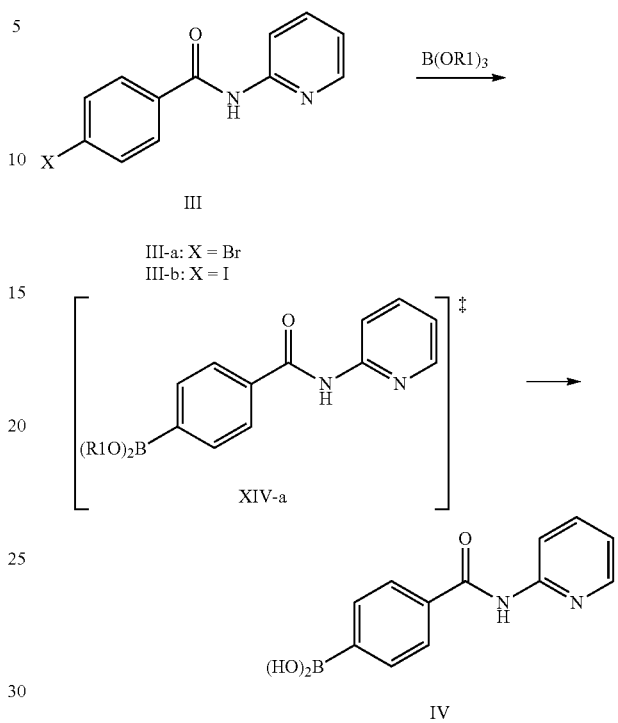

The compound of formula III reacts with organometallic reagent and trialkyl borate to produce the compound of formula IV. Wherein the organometallic reagent is selected from butyl lithium, ethyl lithium, pentyl lithium, phenyl lithium, methyl lithium, cyclohexyl lithium, isopropyl magnesium chloride, isopropyl magnesium bromide and mixtures thereof; R1 is a substituent selected from the group consisting of R1 is C1-20 alkyl or benzyl, preferably methyl, ethyl, propyl, isopropyl and benzyl. More preferably, wherein R1 is isopropyl; the organometallic reagent is n-butyllithium. The reactant, the organometallic reagent and alkyl borate, were screened. Since the amide moiety of compound III might react with organolithium or Gringard reagent before the halogen-metal exchange, or the amide might quench the aryl lithium or aryl Gringard reagent as a proton donor, two compounds with protecting groups at the amide of compound III were prepared and subjected to the reaction. The results are summarized in the following table:

| Entry | Reaction condition | Result |
|---|---|---|
| 1 | 1. iPrMgCl, LiCl, compound III-a; | Almost no reaction |
| 2 | 1. iPrMgCl, n-BuLi, compound III-a; 2. B(O$^i$Pr)$_3$; | 45% yield |
| 3 | 1. n-BuLi, compound III-a; 2. B(O$^i$Pr)$_3$; | 50% yield |
| 4 | 1. NaH, compound III-a; 2. n-BuLi; 3. B(O$^i$Pr)$_3$; | 29% yield |
| 5 | 1. LiHMDS, compound III-a; 2. n-BuLi; 3. B(O$^i$Pr)$_3$; | Almost no reaction |
| 6 | 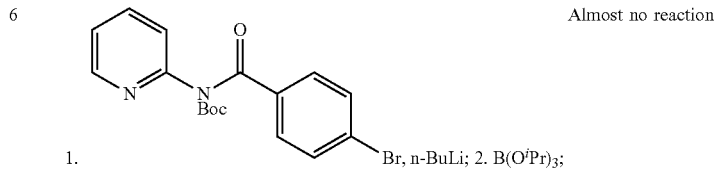 1. ...Br, n-BuLi; 2. B(O$^i$Pr)$_3$; | Almost no reaction |

-continued

| Entry | Reaction condition | Result |
|---|---|---|
| 7 | 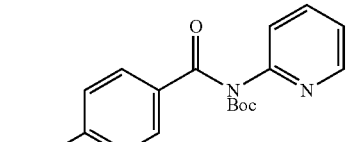  1. Br⟨aryl⟩, n-BuLi; 2. (O^iPr)₃; | Almost no reaction |
| 8 | 1. compound III-a, B(O^iPr)₃; 2. n-BuLi; | 90% yield |

Normally, such reaction starts with halogen-metal exchange by mixing the aryl halide with organometallic reagent, followed by the addition of trialkylborate. It did not work well in the case of compound III as shown in the above table. The amide functionality of the compound III either reacted with organometallic reagent before the halogen-metal exchange occurring or quench the aryl lithium or aryl Gringard reagent by providing a proton, making the reaction not practical. It was unexpectedly found that changing the addition order of the reactants afforded high yield of compound IV. Unexpected high yield was obtained by adding organolithium to a mixture of compound III and trialkylborate under low temperature. The result is shown in the entry 8 of the above table.

Synthesis the Compound of Formula XIV-a or XIV-b from the Compound of Formula IV:

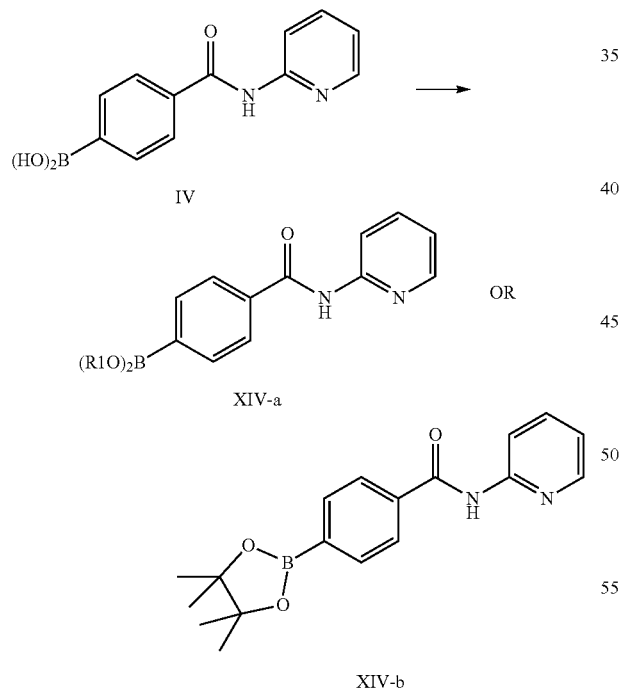

The compound of formula IV reacts with alcohol to produce the compound of formula XIV-a or XIV-b. Wherein, alcohol is selected from methanol, ethanol, propanol, isopropanol, and pinacol. More preferably, alcohol is methanol or pinacol. R1 is a substituent selected from the group consisting of R1 is C1-20 alkyl or benzyl, preferably methyl, ethyl, propyl, isopropyl and benzyl.

The present application provides a process for the preparation of the compound of formula XI:

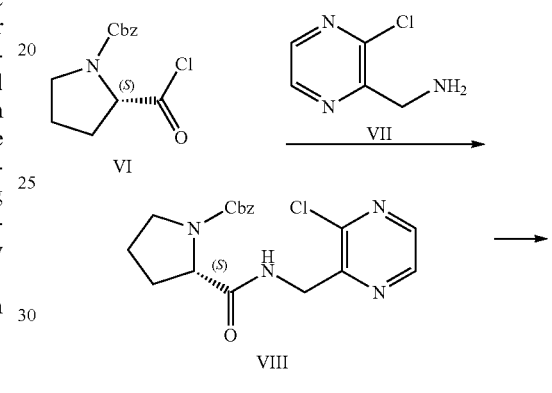

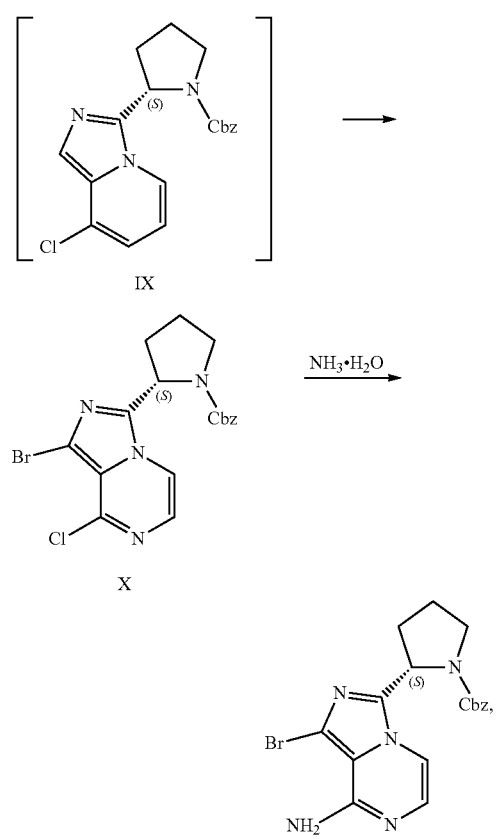

In a specific embodiment, the reaction conditions for each reaction step are detailed below:

Synthesis the Compound of Formula VIII from the Compound of Formula VI and Compound of Formula VII:

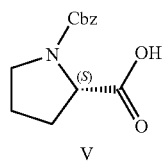
V

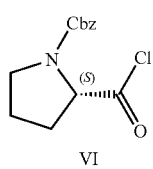 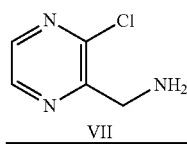
VI    VII

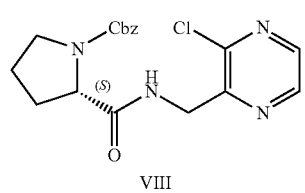
VIII

The compound of formula V reacts with oxalyl chloride to form the compound of formula VI. The compound of formula VI reacts with the compound of formula VI or its salt to produce the compound of formula VIII. Wherein, the equivalent of oxalyl chloride versus the compound of formula V is from 0.8 to 10. More preferably, the equivalent of oxalyl chloride versus the compound of formula V is from 1.5 to 3. The chiral impurity of the compound of formula VIII is not more than 2%. More preferably, the chiral impurity of the compound of formula VIII is not more than 0.5%. The common problems of coupling reagents, such as BOP reagent, PyBOP, HBTU, TBTU, EDCl, are high cost and low atomic economy. Such reaction always generates a large amount of by-product. The acid chloride method is not often used for amide formation from an enantiomer pure amino acid because of the racemization problem. An unusual condition was developed using oxalyl chloride to form acid chloride while the racemization was well suppressed.

Synthesis the Compound of Formula X from the Compound of Formula VIII:

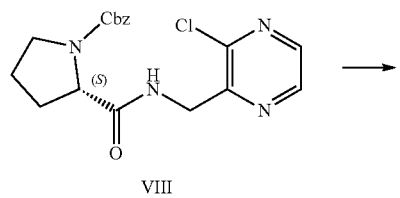
VIII

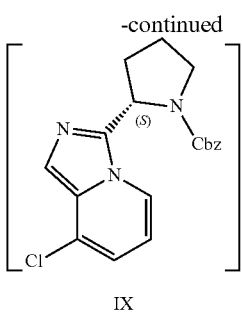
IX

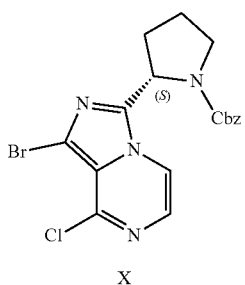
X

The compound of formula VIII reacts with dehydrating reagent to afford the compound of formula IX. The compound of formula IX was treated with bromination reagent to produce the compound of formula X. Wherein the solvent is selected from N,N-dimethylformamide, N,N-dimethylacetamide, acetonitrile, tetrahydrofuran, methyltetrahydrofuran, toluene, xylene, dioxane, dimethyl sulfoxide, N-methylpyrrolidone, sulfolane, methylene chloride and mixtures thereof; the dehydrating reagent is selected from phosphorus oxychloride or phosphorus pentachloride.

Synthesis the Compound of Formula XI from the Compound of Formula X:

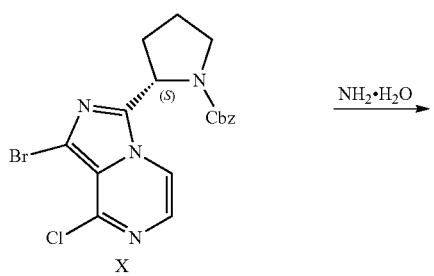
X

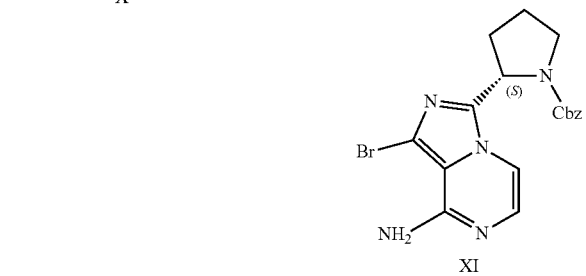
XI

The compound XI is prepared by reacting the compound of formula X with aqueous ammonia in solvent. The solvent is selected from N,N-dimethylformamide, N,N-dimethylacetamide, acetonitrile, isopropanol, tert-butanol, tetrahydrofuran, methyltetrahydrofuran, toluene, xylene, dioxane, dimethyl sulfoxide, N-methylpyrrolidone, sulfolane, methylene chloride and mixtures thereof. More preferably, the solvent is isopropanol.

The present application provides a process for the preparation of acalabrutinib (the compound of formula XV:

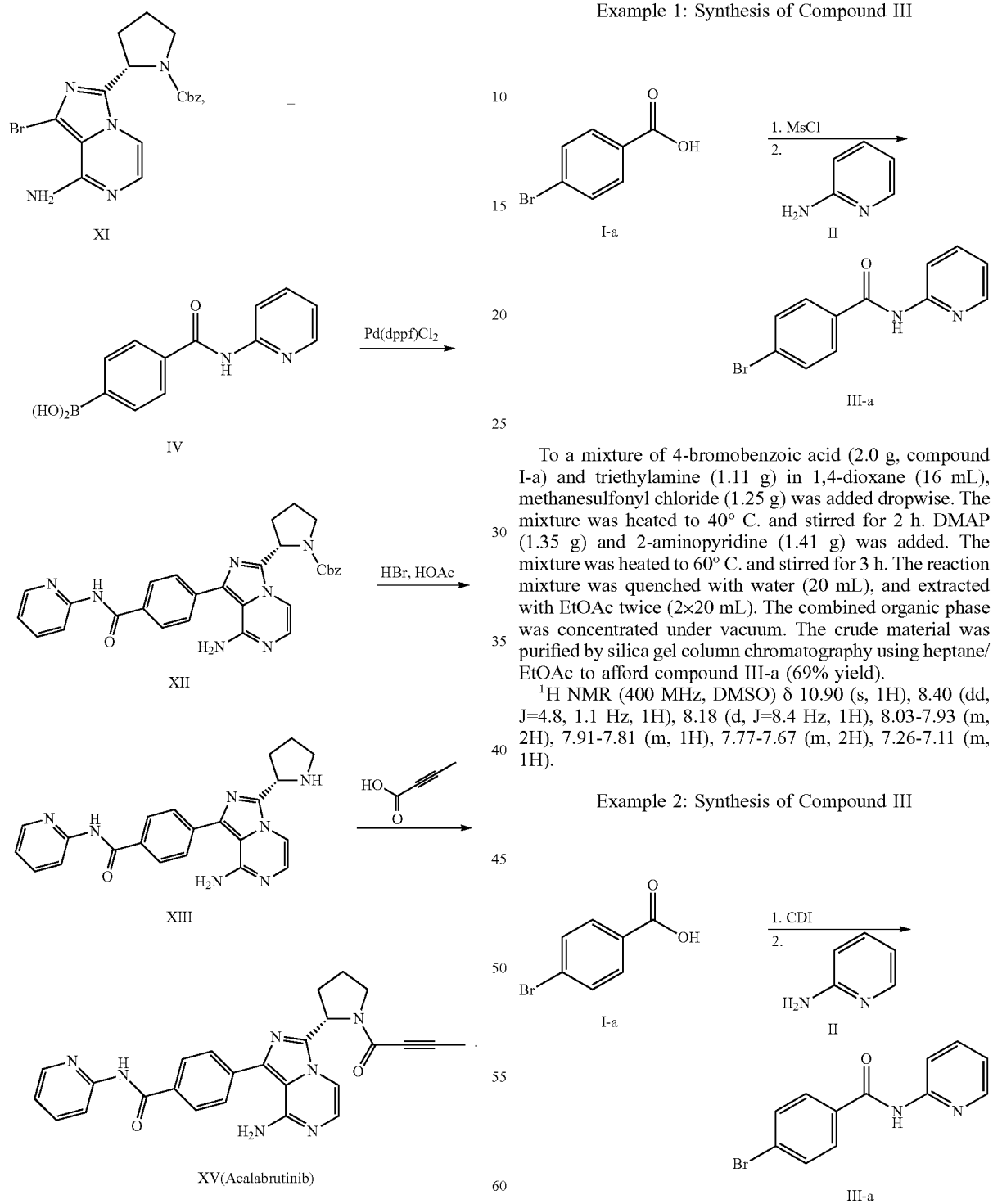

The synthetic route of the present invention provides a cost-effective and scalable method for the preparation of acalabrutinib and two intermediates of formula IV, formula XI.

DETAILED DESCRIPTION OF THE PRESENTLY PREFERRED EMBODIMENTS

EXAMPLES

Example 1: Synthesis of Compound III

To a mixture of 4-bromobenzoic acid (2.0 g, compound I-a) and triethylamine (1.11 g) in 1,4-dioxane (16 mL), methanesulfonyl chloride (1.25 g) was added dropwise. The mixture was heated to 40° C. and stirred for 2 h. DMAP (1.35 g) and 2-aminopyridine (1.41 g) was added. The mixture was heated to 60° C. and stirred for 3 h. The reaction mixture was quenched with water (20 mL), and extracted with EtOAc twice (2×20 mL). The combined organic phase was concentrated under vacuum. The crude material was purified by silica gel column chromatography using heptane/EtOAc to afford compound III-a (69% yield).

$^1$H NMR (400 MHz, DMSO) δ 10.90 (s, 1H), 8.40 (dd, J=4.8, 1.1 Hz, 1H), 8.18 (d, J=8.4 Hz, 1H), 8.03-7.93 (m, 2H), 7.91-7.81 (m, 1H), 7.77-7.67 (m, 2H), 7.26-7.11 (m, 1H).

Example 2: Synthesis of Compound III

To a round-bottom flask was added 4-bromobenzoic acid (20.0 g, compound I-a), 1,1'-Carbonyldiimidazole (CDI, 19.34 g) and toluene (200 mL). The mixture was heated to 60° C. and stirred for 2 h. 2-Aminopyridine (14.04 g) was added. The mixture was heated to 100° C. and stirred for 4 h. The reaction mixture was washed with saturated Na₂CO₃ aqueous solution, water (twice), and brine. The organic phase was concentrated to 100 mL, cooled to 0~5° C., and then stirred for 1 h. After filtration and drying, compound III-a was obtained as a white solid (23 g, 84% yield).

Example 3: Synthesis of Compound IV

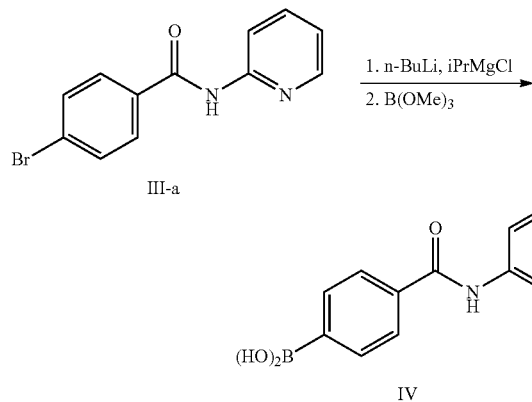

To a round-bottom flask was added i-PrMgCl solution in THF (10 mL, 2 M) and THF (20 mL). The mixture was cooled to −20~-30° C. n-BuLi solution in n-hexane (16.4 mL, 2.5 M) was added dropwise. After 10 min, a solution of compound III-a (5.00 g) in THF (35 mL) was added into the mixture at −20~-30° C. and stirred for 20 min. Trimethyl borate (3.75 g) was added at −20~-30° C. The reaction mixture was stirred for 16 h at this temperature. The reaction mixture was quenched with saturated NH₄Cl aqueous solution (50 mL), and extracted with EtOAc three times. The combined organic phase was concentrated and concentrated under vacuum. The crude material was purified by silica gel column chromatography using DCM/MeOH to afford compound IV (2.00 g, 45.8% yield).

¹H NMR (400 MHz, DMSO) δ 10.75 (s, 1H), 8.52-8.36 (m, 1H), 8.35-8.17 (m, 2H), 8.11-7.79 (m, 5H), 7.24-7.12 (m, 1H).

Example 4: Synthesis of Compound IV

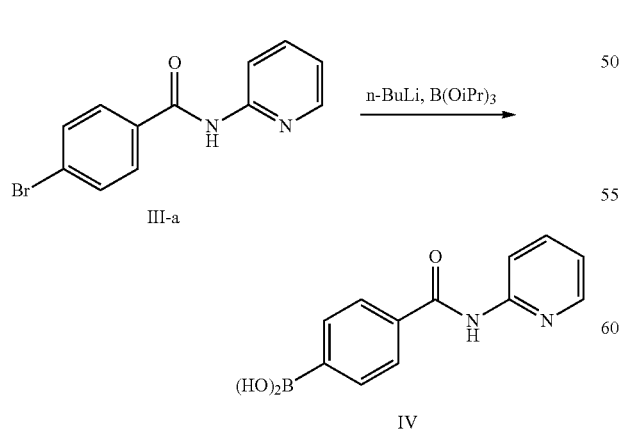

To a round-bottom flask was added compound III-a (1.98 g) and THF (20 mL). The mixture was cooled to −60~-70° C. n-BuLi solution in n-hexane (6.8 mL, 2.5 M) was added at −60~-70° C., followed by addition of triisopropyl borate (2.72 g). After completion of the reaction, saturated NH₄Cl aqueous solution (100 mL) was added to quench the reaction. The mixture was extracted with EtOAc twice (2×200 mL). The combined organic phase was washed with brine, and concentrated under vacuum. The crude material was purified by reslurrying in EtOAc/Heptane to get compound IV (0.92 g, 53% yield).

Example 5: Synthesis of Compound IV

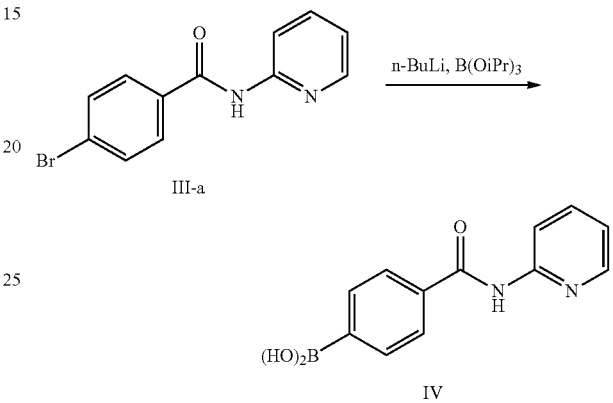

To a mixture compound III-a (1.01 g), triisopropyl borate (1.36 g) and THF (10 mL) at −60~-70° C. n-BuLi solution in n-hexane (6 mL, 2.5 M) was added slowly. Additional triisopropyl borate (0.81 g, 1 mL) was added simultaneously. After completion of the reaction, saturated NH₄Cl aqueous solution (50 mL) was added to quench the reaction. The mixture was extracted with EtOAc twice (2×100 mL). The combined organic phase washed with brine. The organic phase was concentrated under vacuum. The crude material was purified by reslurrying in EtOAc/Heptane to afford compound IV (0.76 g, 86% yield).

Example 6: Synthesis of Compound IV

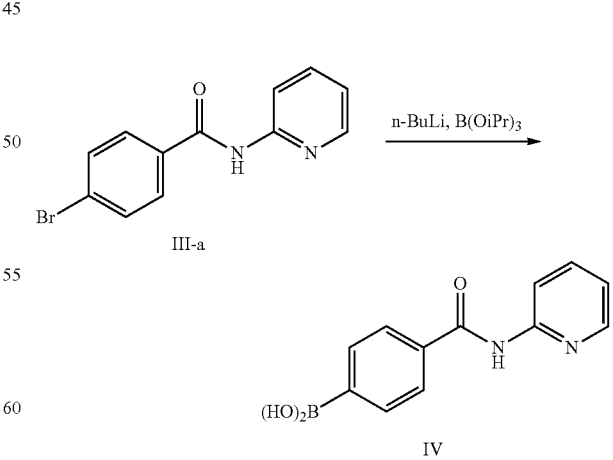

To a mixture of compound III-a (50 g), triisopropyl borate (84.9 g) and THF (500 mL) at −60~-70° C., n-BuLi solution in n-hexane (378 mL, 2.5 M) was added. After completion of the reaction, 10% NH₄Cl aqueous solution (500 mL) was added to quench the reaction. The mixture was extracted with EtOAc (2×500 mL). The combined organic phase was washed with brine and concentrated under vacuum. The crude material was purified by reslurrying in IPAc/Heptane to afford compound IV (39 g, 90% yield).

Example 7: Synthesis of Compound XIV-b

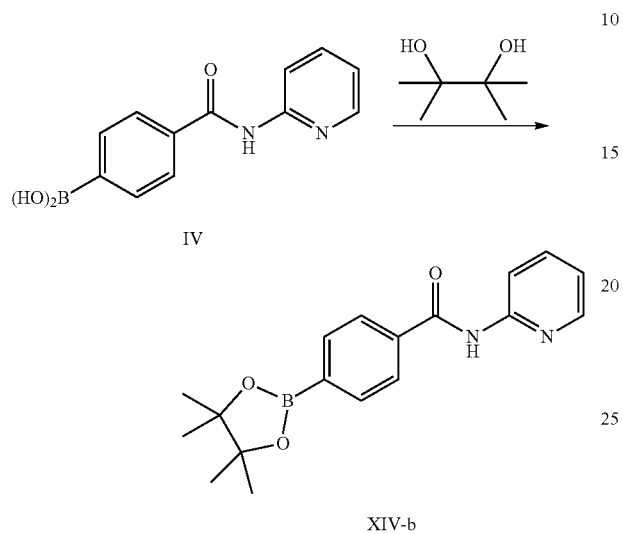

To a round-bottom flask was added compound IV (17.2 g), pinacol (12.6 g) and methanol (70 mL). The mixture was stirred for 2 h at 40~50° C. The reaction mixture was cooled to 5° C. and stirred for 1 h. After filtration and drying, compound XIV-b was obtained as white solid (14.5 g, 63% yield).

$^1$H NMR (400 MHz, DMSO) δ 10.82 (s, 1H), 8.40-8.38 (m, 1H), 8.23-8.20 (m, 1H), 8.06-8.02 (m, 2H), 7.87-7.77 (m, 3H), 7.18-7.14 (m, 1H), 1.31 (s, 12H).

Example 8: Synthesis of Compound IV

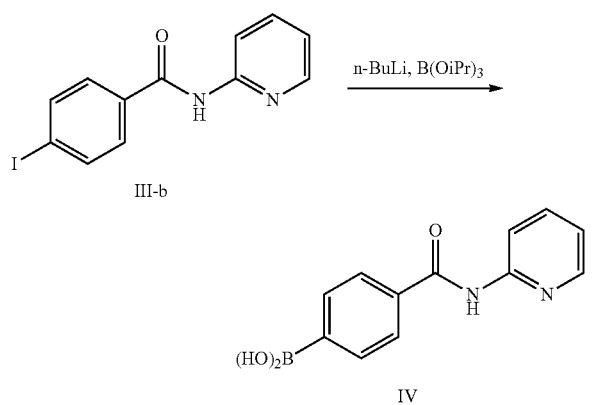

To a mixture of compound III-b (2.00 g), triisopropyl borate (2.90 g) and THF (20 mL) at −60~-70° C., n-BuLi solution in n-hexane (8.64 mL, 2.5 M) was added. After completion of the reaction, saturated NH$_4$Cl aqueous solution (50 mL) was added to quench the reaction. The mixture was extracted with EtOAc (2×100 mL). The combined organic phase was washed with brine and concentrated under vacuum. the crude material was purified by reslurrying in EtOAc/Heptane to afford compound IV (0.92 g, 62% yield).

Example 9: Synthesis of Compound VIII

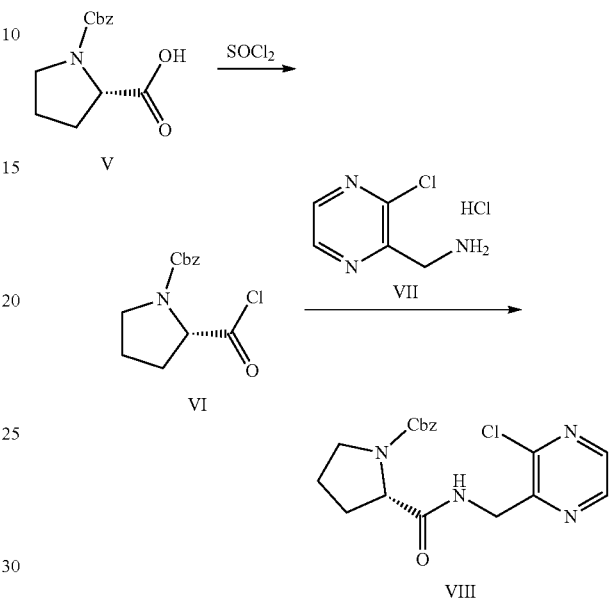

To a mixture of compound V (5.0 g), dichloromethane (DCM, 50 mL) and DMF (0.25 mL) in a 100 mL three-neck flask, SOCl$_2$ (9.6 g, 4 eq) was added. The reaction mixture was stirred at RT. After completion of the reaction, the solvent was removed by concentration. DCM (20 mL) was added to prepare a solution of compound VI in DCM.

To a mixture of compound VII (3 g), DCM (30 mL, 6 vol) and TEA (12.2 g, 6 eq) in a 100 mL three-neck flask at 0~10° C., the solution of compound VI in DCM obtained in above step was added dropwise. The reaction mixture was warmed to RT. After the reaction was completed, water (100 mL, 20 vol) was added to quench the reaction. The mixture was extracted with DCM (2×50 mL). The combined organic phase was washed with saturated NH$_4$Cl aqueous solution (50 mL, 10 vol) and saturated NaHCO$_3$ aqueous solution (50 mL, 10 vol), and concentrated under vacuum. The crude material was recrystallized from IPAc/Heptane to afford compound VIII (6.0 g, 96% yield, 99.7% chiral purity).

NMR sample was obtained by column chromatography:
$^1$H NMR (400 MHz, DMSO) δ 8.65-8.35 (m, 3H), 7.42-7.20 (m, 5H), 5.13-4.97 (m, 2H), 4.63-4.40 (m, 2H), 4.35-4.22 (m, 1H), 3.55-3.35 (m, 2H), 2.25-2.05 (m, 1H), 1.97-1.74 (m, 3H).

Example 10: Synthesis of Compound VIII

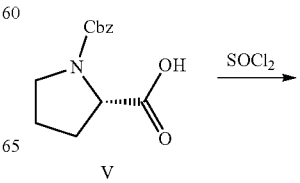

-continued

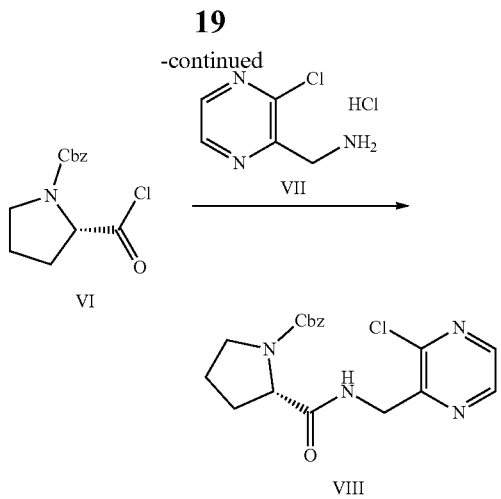

To a 1000 mL three-necked bottom flask was added compound V (30 g), DCM (300 mL) and DMF (0.5 mL). SOCl$_2$ (28 g, 2 eq) was added and the reaction mixture was stirred at RT. After completion of the reaction, the solvent was removed by concentration. The residual was added toluene (60 mL) and evaporated in vacuo. DCM (120 mL) was added to obtain a solution of compound VI in DCM.

To a mixture of compound VII (18 g), DCM (180 mL) and TEA (73 g, 6 eq) in a 1000 mL three-neck flask at 0~10° C. the solution of compound VI in DCM obtained from the above step was added dropwise. The reaction mixture was warmed to RT. After the reaction was completed, water (600 mL) was added to quench the reaction. The mixture was extracted with DCM (2×300 mL). The combined organic phase was washed with saturated NH$_4$Cl aqueous solution (300 mL) and saturated NaHCO$_3$ aqueous solution (300 mL), and Concentrated under vacuum. The crude material was purified by silica gel column chromatography and recrystallized from IPAc/Heptane to afford compound VIII (28.5 g, 76% yield, 92.7% chiral purity).

Example 11: Synthesis of Compound VIII

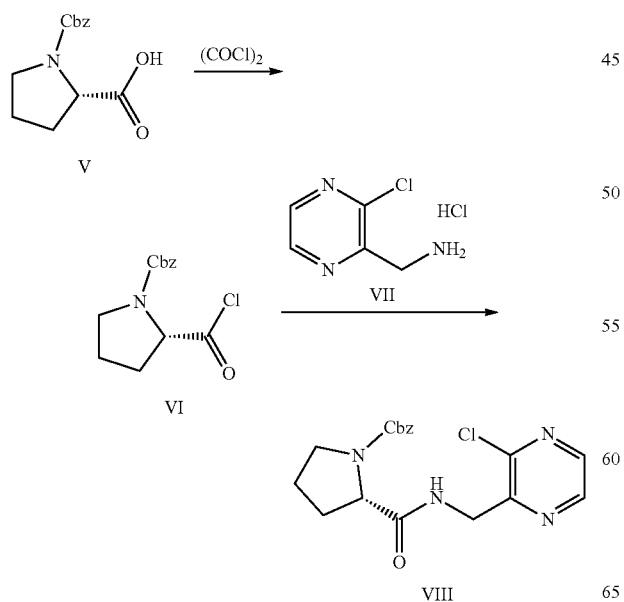

To a mixture of compound V (49.8 g), DCM (500 mL) and DMF (5 mL) in a 500 mL three-neck flask, oxalyl chloride (38 g, 1.5 eq) was added at 0~10° C. The reaction mixture was warmed to RT. After completion of the reaction, the solvent was removed by concentration. DCM (200 mL) was added to obtain the compound VI solution in DCM.

To a mixture of compound VII (30 g), DCM (240 mL) and TEA (6 eq) in a 1000 mL three-neck flask at 0~10° C., the solution of compound VI in DCM obtained from the above step was added dropwise, the reaction mixture was warmed to RT. After the reaction was completed, water (300 mL) was added to quench the reaction. The organic phase was washed with 1N HCl aqueous solution (500 mL), saturated NaHCO$_3$ aqueous solution (500 mL) and water (500 mL). The organic phase was concentrated under vacuum. The crude product was recrystallized from IPAc/Heptane to afford compound VIII (61 g, 98% yield, 99.7% chiral purity).

Example 12: Synthesis of Compound XI

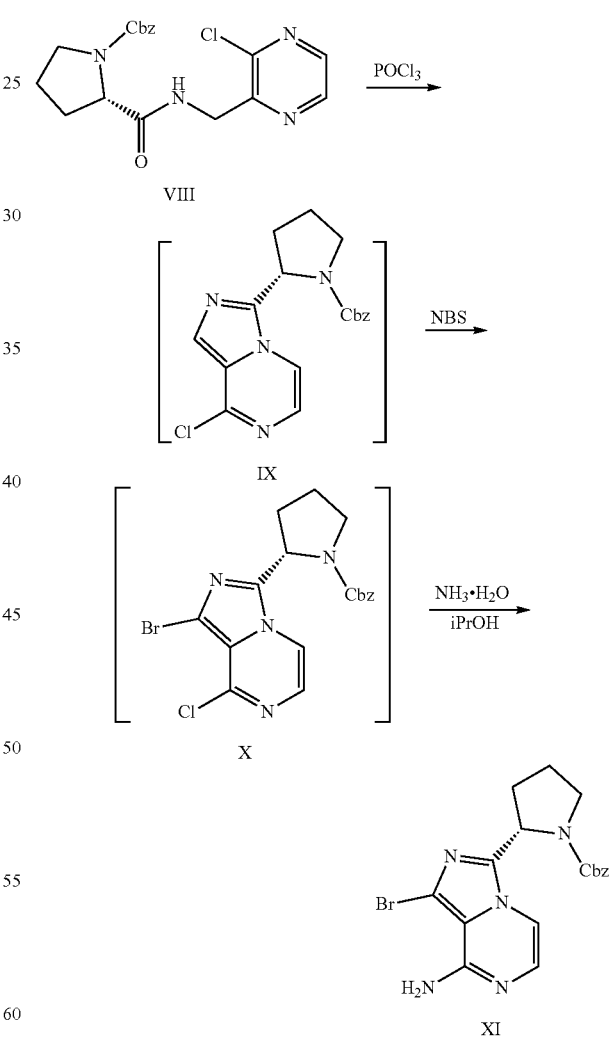

To a 250 mL round-bottom flask was added compound VIII (5 g), DCM (125 mL) and DMF (1 eq). The mixture was cooled to 0~10° C. POCl$_3$ (10 g, 5 eq) was added. The reaction mixture was warmed to RT. After the reaction was completed, ice water (50 mL) and saturated NaHCO$_3$ aqueous solution (50 mL) were added to quench the reaction. The organic phase was washed with saturated NH₄Cl aqueous solution (50 mL) to give a solution of compound IX in DCM.

After being dried by azeotropic distillation, the solution of compound IX solution in DCM was added NBS (2.1 g, 0.9 eq). After reaction completion, the reaction mixture was washed with saturated NH₄Cl aqueous solution (30 mL), saturated NaHCO₃ aqueous solution (30 mL) and water (50 mL) to give the compound X solution in DCM. The solvent evaporated in vacuo to give crude compound X.

The crude compound X was transferred to a pressure reactor. Isopropanol (100 mL) and ammonium hydroxide (50 mL) were added. The mixture was heated to 120° C. The solvents were removed after reaction completion. IPAc and water were added. The mixture was extracted with 1 N HCl aqueous solution twice. The pH of the combined aqueous phase was adjusted to 8~9 with 30% NaOH aqueous solution. The mixture was extracted with IPAc. Recrystallization in IPAc/Heptane afforded compound XI (3.53 g, 63.6% overall yield).

¹HNMR (400 MHz, DMSO) δ 7.68 (m, 1H), 7.44-7.07 (m, 4H), 6.96 (m, 1H), 6.76 (d, J=7.0 Hz, 1H), 6.65 (s, 2H), 5.32 (ddd, J=10.8, 7.5, 4.0 Hz, 1H), 5.12-4.64 (m, 2H), 3.54 (ddd, J=23.5, 15.8, 8.7 Hz, 2H), 2.38-2.06 (m, 2H), 2.04-1.83 (m, 2H).

Example 13: Synthesis of Compound XI

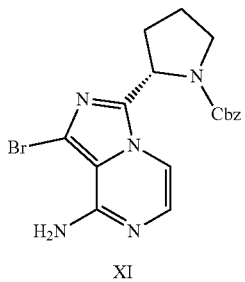

XI

To a mixture of compound VIII (5 g) and acetonitrile (30 mL) at 50~60° C., PCl₅ (5 g, 1.8 eq) was added. The reaction mixture was stirred for 20 h at 50~60° C. DCM (25 mL) and water (25 mL) were added to quench the reaction. The organic phase was washed with water (25 mL) and concentrated to about 15 mL. DCM (35 mL) was added to give a solution of compound IX in DCM.

The solution of compound IX in DCM was added dibromohydantoin (1.7 g, 0.45 eq) and stirred for 2 h at 20~30° C. The reaction mixture was washed with water (25 mL) and concentrated under vacuum. The crude material was purified by recrystallization from IPA/H₂O to give compound X (5.0 g).

To a pressure reactor, compound X (3.0 g), isopropanol (54 mL) and ammonium hydroxide (18 mL) were added. The mixture was heated to 120° C. After reaction completion of the, the solvent was removed. IPAc and 1 N HCl aqueous solution were added. The layers were separated. The pH of the aqueous phase was adjusted to >10 with 30% NaOH aqueous solution and extracted with DCM. The DCM phase was concentrated. The material was purified by recrystallization from MeOH/H₂O to give compound XI (1.17 g, 35.1% overall yield).

Example 14: Synthesis of Compound XV

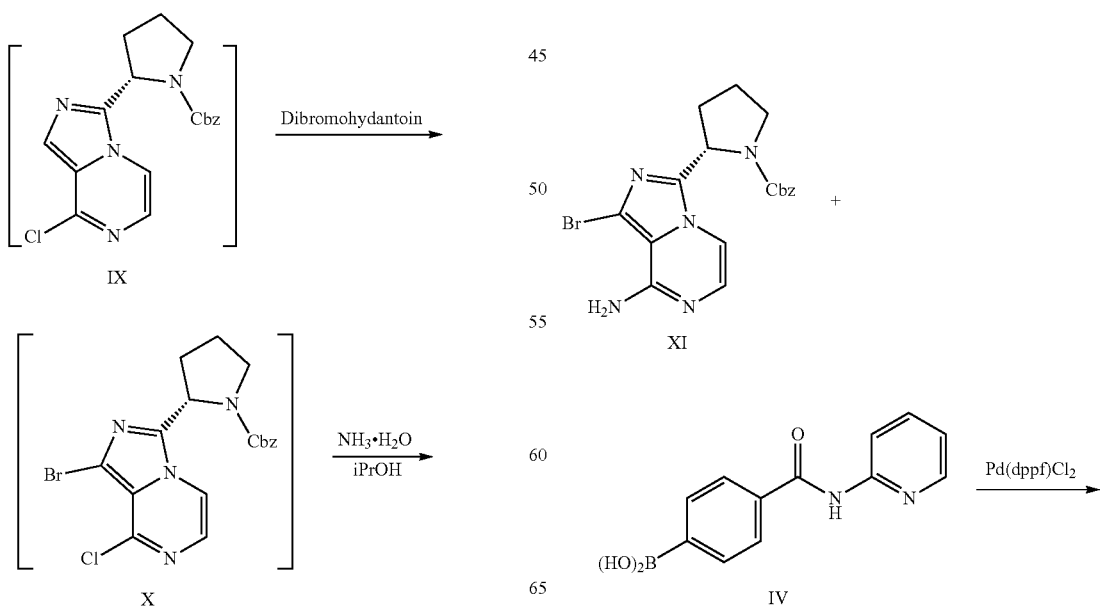

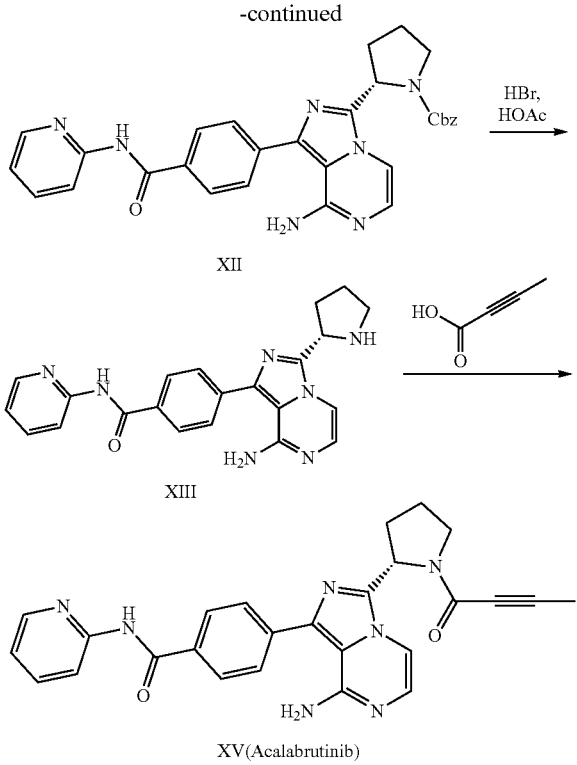

A mixture of compound XI (4.14 g, 10 mmol), compound IV (2.66 g, 11 mmol), dioxane (34 mL) and K$_2$CO$_3$ aqueous solution (4.14 g K$_2$CO$_3$ in 15 mL water) was added Pd(dppf)Cl$_2$ (73 mg, 0.1 mmol) under nitrogen. The mixture was stirred for 3 h at 90~100° C. The organic phase was separated and concentrated. The residue was purified by silica gel column chromatography using heptane/EtOAc to afford compound XII (4.9 g, 92% yield).

To a round-bottom flask was added compound XII (2.4 g), acetic acid (12 mL) and HBr (33% in acetic acid, 12 mL). The mixture was stirred for 2 h at 20~30° C. Water (300 mL) and DCM (100 mL) was added. The aqueous phase was separated and washed with DCM (100 mL). The aqueous phase was adjusted to pH>10 with 30% NaOH aqueous solution and extracted with DCM (150 mL). The DCM phase was concentrated to give compound XIII (1.64 g, 91% yield).

To a round-bottom flask was added compound XIII (0.50 g, 1.25 mmol), 2-butynoic acid (0.11 g, 1.31 mmol), HATU (0.48 g, 1.25 mmol), DCM (10 mL) and triethylamine (0.50 g, 5 mmol). The mixture was stirred for 3 h at 20~30° C. The reaction mixture was washed with water (5 mL) and concentrated. The residue was purified by silica gel column chromatography using DCM/MeOH to afford compound XV (0.5 g, 90% yield).

$^1$H NMR (400 MHz, DMSO) δ 10.82 (s, 1H), 8.42-8.39 (m, 1H), 8.26-8.15 (m, 3H), 7.90-7.73 (m, 4H), 7.21-7.11 (m, 2H), 6.25-6.05 (m, 2H), 5.75-5.40 (m, 1H), 3.90-3.55 (m, 2H), 2.47-2.20 (m, 2H), 2.20-2.10 (m, 1H), 2.07-1.90 (m, 3H), 1.63 (s, 1H).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

We claim:

1. A process for preparation of compound IV from compound of formula III,

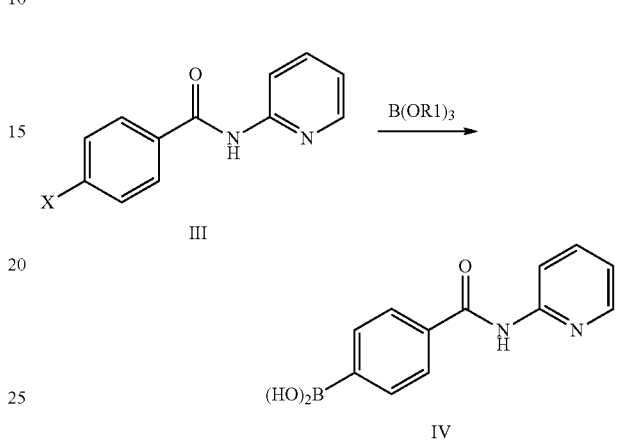

comprising reacting the compound of formula III with an organometallic reagent and trialkyl borate to produce the compound of formula IV, wherein R1 is C$_{1-20}$ alkyl or benzyl, and X is Br or I.

2. The process of claim 1, wherein R1 is a substituent selected from the group consisting of methyl, ethyl, propyl, isopropyl and benzyl; and X is Br or I.

3. The process of claim 2, wherein R1 is isopropyl; and X is Br.

4. The process of claim 1, wherein organometallic reagent is selected from the group consisting of butyl lithium, ethyl lithium, pentyl lithium, phenyl lithium, methyl lithium, cyclohexyl lithium, isopropyl magnesium chloride, isopropyl magnesium bromide and the mixtures thereof.

5. The process of claim 4, wherein organometallic reagent is n-butyllithium.

6. A process for preparation of compound III from compound of formula I and compound of formula II,

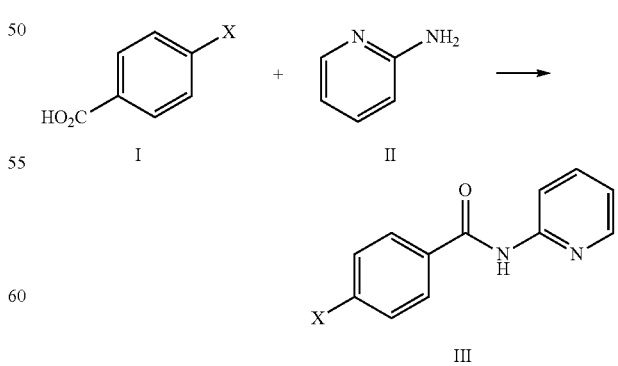

comprising reacting the compound of formula I with an activating reagent and the compound of formula II in a solvent to produce the compound of formula III;

wherein the activating reagent is selected from the group consisting of N,N'-carbonyldiimidazole, methanesulfonyl chloride, p-toluenesulfonyl chloride and p-nitrobenzene sulfonyl chloride; and X is Br or I.

7. The process of claim 6, wherein the solvent is selected from the group consisting of N,N-dimethylformamide, N,N-dimethylacetamide, acetonitrile, tetrahydrofuran, methyltetrahydrofuran, toluene, xylene, dioxane, dimethyl sulfoxide, N-methylpyrrolidone, sulfolane, methylene chloride and mixtures thereof.

8. The process of claim 7, wherein the solvent is selected from the group consisting of tetrahydrofuran, toluene, and dioxane.

9. A process for preparation of compound IV from compound of formula I and compound of formula II,

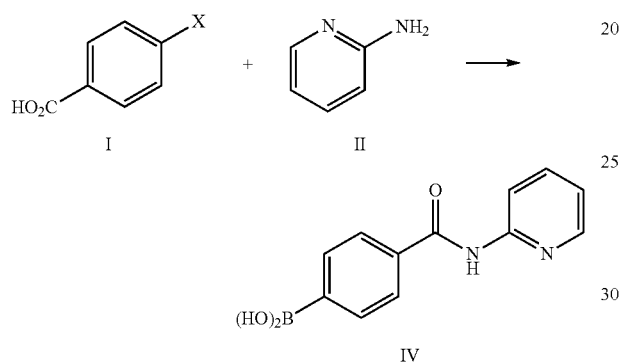

comprising steps of coupling of the compound of formula I and the compound of formula II to produce the compound of formula III; wherein X is Br or I and reacting the compound of formula III with an organometallic reagent and trialkyl borate to produce the compound of formula IV.

10. A process for preparation of compound VIII from compound of formula VI, comprising reacting the compound of formula VI with the compound of formula VII or its salt to produce the compound of formula VIII, where Cbz is carboxybenzyl.

11. The process of claim 10, wherein the compound of formula VI is prepared from compound of formula V and oxalyl chloride,

12. The process of claim 11, wherein the equivalent of oxalyl chloride versus the compound of formula V is from 0.8 to 10.

13. The process of claim 12, wherein the equivalent of oxalyl chloride versus the compound of formula V is from 1.5 to 3.

14. The process of claim 10, wherein the chiral impurity of the compound of formula VIII is not more than 2%.

15. The process of claim 14, wherein the chiral impurity of the compound of formula VIII is not more than 0.5%.

16. A process for preparation of compound X from compound of formula VIII in a solvent, -continued

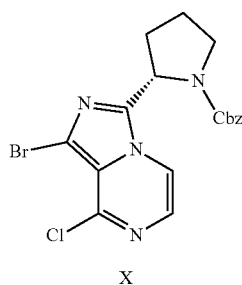

X comprising; reacting the compound of formula VIII

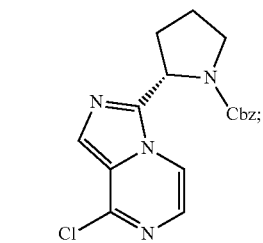

VIII with a dehydrating reagent to produce compound of formula IX

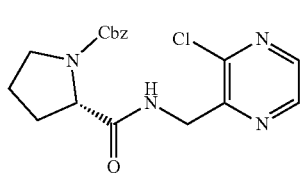

IX and bromination of the compound of formula IX to produce the compound of formula

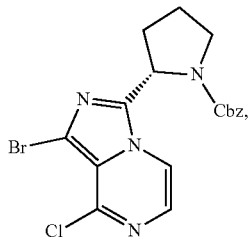

X where Cbz is carboxybenzyl.

17. The process of claim 16, wherein the solvent is selected from the group consisting of N,N-dimethylformamide, N,N-dimethylacetamide, acetonitrile, tetrahydrofuran, methyltetrahydrofuran, toluene, xylene, dioxane, dimethyl sulfoxide, N-methylpyrrolidone, sulfolane, methylene chloride and mixtures thereof.

18. The process of claim 17, wherein the solvent is methylene chloride.

19. A process for preparation of compound XI from compound of formula VIII in a solvent,

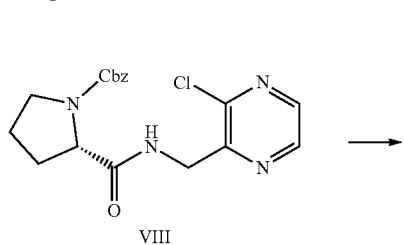

VIII

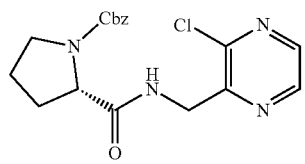

XI comprising reacting the compound of formula VIII

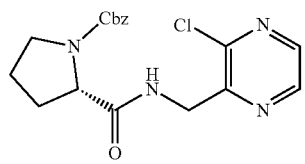

VIII with a dehydrating reagent to produce compound of formula IX

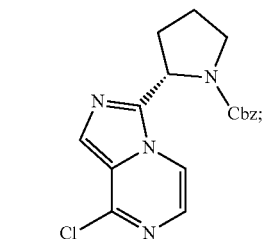

IX and bromination of compound of formula IX to produce the compound of formula X

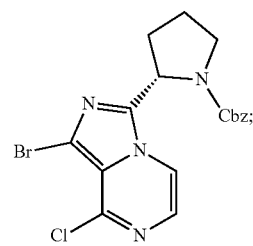

X and reacting the compound of formula X with aqueous ammonia to produce the compound of formula XI

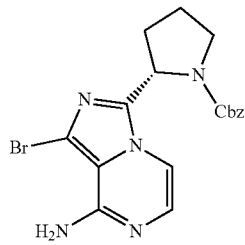

XI where Cbz is carboxybenzyl.

20. A process for preparation of compound XIV-a or XIV-b from compound of formula IV,

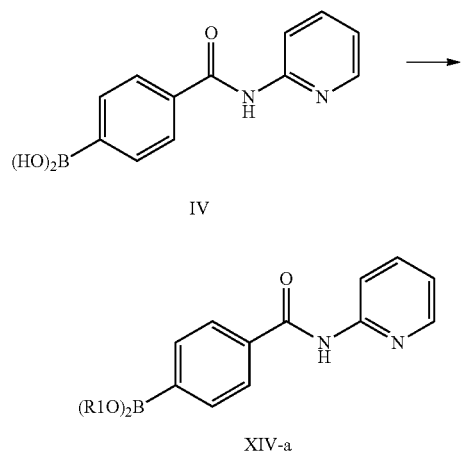

comprising reacting a compound of formula IV with alcohol to produce the compound of formula XIV-a or XIV-b, wherein R1 is $C_{1-20}$ alkyl or benzyl.

21. The process of claim 20, wherein alcohol is selected from the group consisting of methanol, ethanol, propanol, isopropanol, and pinacol; wherein R1 is a substituent selected from the group consisting of methyl, ethyl, propyl and isopropyl.

22. The process of claim 20, wherein alcohol is methanol or pinacol, wherein R1 is methyl.

23. The process for preparation of compound XV from compound of formula I and compound of formula II,

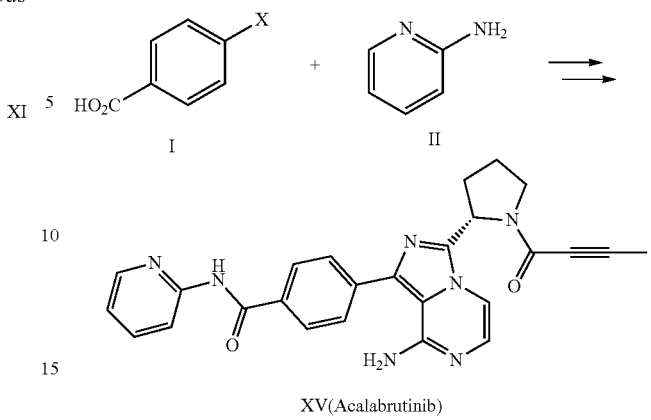

comprising steps of:
1) amide formation of the compound of formula I and the compound of formula II

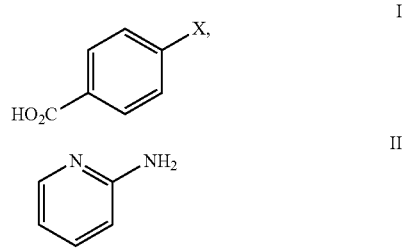

to produce compound of formula wherein X is Br or I

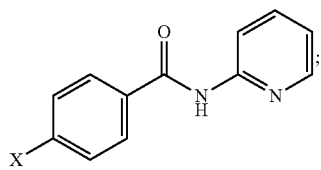

2) reacting the compound of formula III with an organometallic reagent and trialkyl borate to produce compound of formula IV, or derivative compound of formula XIV-a, compound of formula XIV-b

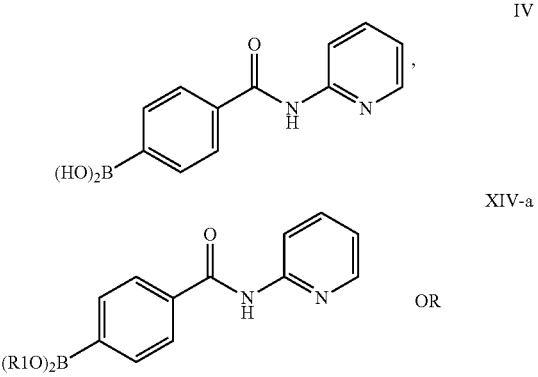

XIV-b

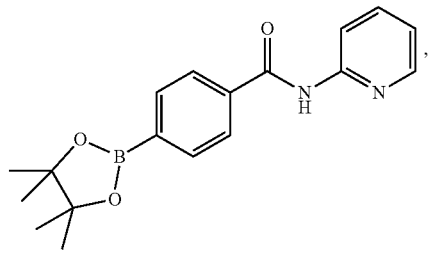

wherein R1 is a substituent selected from the group consisting of methyl, ethyl, propyl, isopropyl and benzyl;

3) reacting the compound of formula IV, or derivative compound of formula XIV-a, or compound of formula XIV-b, with the compound of formula XI by transition-metal catalyzed cross coupling reaction to produce the compound of formula XII, where Cbz is carboxybenzyl

XI

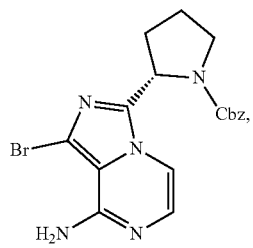

XII

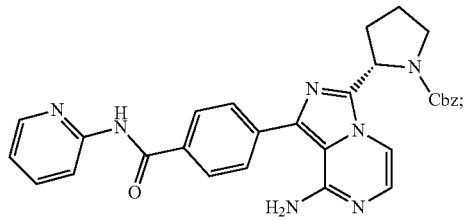

4) removal of Cbz protection group of the compound of formula XII to produce the compound of formula XIII

XIII

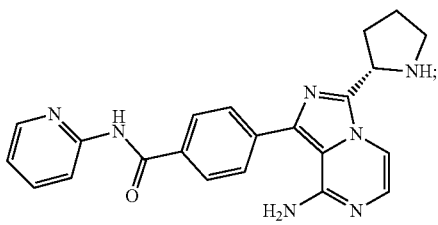

and 5) amide formation of the compound of formula XIII with but-2-ynoic acid to produce the compound of formula XV.

* * * * *